(12) United States Patent
Poulos et al.

(10) Patent No.: US 7,056,945 B1
(45) Date of Patent: Jun. 6, 2006

(54) SELECTIVE INHIBITION OF NEURONAL NITRIC OXIDE SYNTHASE

(75) Inventors: Thomas Poulos, Irvine, CA (US); Huiying Li, Irvine, CA (US); Mack Flinspach, Lake Forest, CA (US)

(73) Assignee: The Regents of the University of California, Oakland, CA (US)

( * ) Notice: Subject to any disclaimer, the term of this patent is extended or adjusted under 35 U.S.C. 154(b) by 272 days.

(21) Appl. No.: 10/463,213

(22) Filed: Jun. 17, 2003

Related U.S. Application Data

(60) Provisional application No. 60/388,898, filed on Jun. 14, 2002.

(51) Int. Cl.
*A61K 31/40* (2006.01)
*A61K 31/16* (2006.01)

(52) U.S. Cl. .................. 514/428; 514/429; 514/614
(58) Field of Classification Search ............. 514/428, 514/429, 614
See application file for complete search history.

(56) References Cited

U.S. PATENT DOCUMENTS

| | | | | |
|---|---|---|---|---|
| 3,896,152 | A * | 7/1975 | Otsuka et al. | 552/7 |
| 6,274,557 | B1 * | 8/2001 | Silverman et al. | 514/19 |
| 6,534,546 | B1 * | 3/2003 | Honda et al. | 514/586 |

OTHER PUBLICATIONS

Griffith, Owen W., et al., Nitric Oxide Synthases: Properties and Cataltic Mechanism, Annual Review Physiol, 1995, 707-736, vol. 57, Annual Review, Inc.
Huang, Hui, et al., Synthesis and Evaluation of Peptidomimetics as Selective Inhibitors and Active Site Probes of Nitric Oxide Synthases, J. Medical Chemistry, 2000, 2938-2945.
Hah, Jung-Mi, et al., Reduced Amide Bond Peptidomimetics. (4S)-N-(4-Amino-5-[aminoalkyl] aminopentyl)-N-nitroguanidines, Potent and Highly Selective Inhibitors of Neuronal Nitric Oxide Synthase, J. Medical Chemistry, 2001, 2667-2670, vol. 44, American Chemical Society.
Silverman, Richard B., et al., Selective Inhibition of Neuronal Nitric Oxide Synthase by Nw-Nitroarginine-and Phenylalanine-Containing Dipeptides and Dipeptide Esters, J. Medical Chemistry, 1997, 2813-2817, vol. 40, American Chemistry Society.
Huang, Hui, et al., N-Nitroarginine-Containing Dipeptide Amides. Potent and Highly Selective Inhibitors of Neuronal Nitric Oxide Synthase, J. Medical Chemistry, 1999, 3147-3153, vol. 42, American Chemistry Society.
Taddei, Stefano, et al., Endothelial Dysfunction in Hypertension, Journal of Cardiovasular Pharmacology, 2001, S11-S14, vol. 38, Supl. 2.
Moncada, S., et al., Nitric Oxide: Physiology, Pathophysiology, and Pharmacology, Pharmacological Reviews, 1991, 109-142, vol. 43, No. 2, The American Society for Pharmacology and Experimental Therapeutics.
Grant, Stephan K., Structural Requirements for Human Inducible Nitric Oxide Synthase Substrates and Substrate Analogue Inhibitors, Biochemistry, 1998, 4174-4180, vol. 37, No. 12, American Chemical Society.
Lee, Younghee, et al., Conformationally-restricted Arginine Analogues as Alternative Substrates and Inhibitors of Nitric Oxide Synthases, Bioorganic & Medical Chemistry, 1999, 1097-1104, vol. 7.
Sachais, Bruce S., Platelet-Endothelial Interactions in Atherosclerosis, Current Atherosclerosis Reports, 2001, 412-416, vol. 3.
Dinerman, J., et al., Molecular Mechanisms of Nitric Oxide Regulation Potential Relevance to Cardiovascular Disease, 1993, 217-222, vol. 73, No. 2.
Dawson, V. L, et al., Nitric oxide in neurodegeneration, Progress in Brian Research, 1998, vol. 118, 215-229.
Kerwin, Jr., James F., et al., Nitric Oxide: A New Paradigm for Second Messengers, Journal of Medical Chemistry, 1995, 4343-4362, vol. 38, No. 22, the American Chemical Society.
Masters, B.S.S., et al., Neuronal nitric Oxide Synthase, A Modular Enzyme formed by convergent evolution: structure studies of a cysteine thiolate-liganded heme protein that hydroxylates L-areginine to produce NO as a cellular signal, Cythochromes, 1996, 552-558, vol. 10, The FASEB Journal.
Cho, C.H., Current roles of nitric oxide in gastrointestinal disorders, Journal of Physiology, 2001, 253-256, vol. 95, Elsevier.

* cited by examiner

*Primary Examiner*—Raymond J. Henley, III
(74) *Attorney, Agent, or Firm*—Robert D. Buyan; Stout, Uxa, Buyan & Mullins, LLP

(57) ABSTRACT

Compositions, prodrugs and methods for inhibiting neural Nitric Oxide Synthase (nNOS). By inhibiting nNOS, the compounds, prodrugs and methods of the presnet invention are useable to treat or prevent disorders in human or veterinary patients that are caused, mediated or agrevated by Nitric Oxide within the body.

14 Claims, 4 Drawing Sheets

DIP1

DIP2

DIP3

US 7,056,945 B1

SELECTIVE INHIBITION OF NEURONAL NITRIC OXIDE SYNTHASE

RELATED APPLICATION

This application claims the benefit of U.S. Provisional Application Ser. No. 60/388,898 filed Jun. 14, 2002, which is expressly incorporated herein by reference.

STATEMENT REGARDING FEDERALLY SPONSORED RESEARCH OR DEVELOPMENT

This invention was made with Government support under Grant No. GM57353, awarded by the National Institute of Health. The Government has certain rights in this invention.

FIELD OF THE INVENTION

The invention describes novel compounds that selectively inhibit neuronal Nitric Oxide Synthase (nNOS) over other isoforms of this enzyme and related methods od synthesis and use.

BACKGROUND

Enzymes are generally important molecules in living systems considering that they are responsible for the catalysis of the synthesis and/or degradation of biomolecules. As used herein, the term "enzyme" means any molecule that catalyzes or promotes a biochemical reaction without itself being changed or consumed by the reaction. Enzymes work by lowering the activation energy for a chemical reaction and are specific for particular reactions. Enzyme specificity is defined by the molecular shape and/or charge at the active site of a substrate and thus, the enzymes and the substrates fit together like compatible puzzle pieces. Enzymes are generally thought to be protein-based, although there is research to suggest that several enzymes may be something other than protein-based (RNA molecules that catalyze its own splicing). As used herein, the term "substrate" means the substance upon which an enzyme acts. Also as used herein, the phrase "active site" means the region or portion of an enzyme that interacts with the substrate. The three dimensional conformation of amino acids at the active site determines the specificity of the substrate binding. Rudin, Norah, *Dictionary of Modern Biology*, Barron's Educational Series, Inc. (Hauppauge, N.Y.), 1997.

According to International Union of Biochemistry and Molecular Biology (IUBMB), enzymes can be classified into following six major classes: a) Oxidoreductases catalyze oxidation-reduction reactions and include dehydrogenases (lactate dehydrogenase, acyl CoA dehydrogenase), oxidases (glucose oxidase), peroxidases (Horseradish peroxidase), oxygenases (lactate 2-monooxygenase), and reductases (ketoacyl-ACP reductase); b) transferases catalyze C-, N-, P-, S-containing functional group transfers and include kinases (glucokinase, tyrosine kinase), aminotransferases (aspartate and glutamate aminotransferases), and thiolases (β-ketothiolase); c) hydrolases catalyze hydrolysis reactions involving esters, anhydrides, peptide bonds, glycosides and include peptidases (trypsin, carboxypeptidase), glycosidases (α-glucosidase, amylase, maltase), lipases (triacylglycerol lipase), phosphatases (fructose-1,6-bisphosphatase) and esterases (Cholesterol esterase, acetylcholinesterase, phosphodiesterase); d) lyases catalyze elimination (or addition) of groups to form (or break) double bonds and include synthases (citrate synthase), decarboxylases (pyruvate decarboxylase) and dehydratases (fumarase, aldolase); e) isomerases catalyze reactions that alter structure, not composition (optical, geometric, or structural isomers) and include isomerases (glucose-6-phosphate isomerase, ribulose phosphate epimerase) and mutases (phosphoglycerate mutase); and f) ligases catalyze coupling of two compounds along with hydrolysis of a phosphoric anhydride bond and include synthetases (glutamine synthetase), carboxylases (pyruvate carboxylase) and polymerases (DNA polymerase).

Enzyme inhibitors are those molecules or groups of molecules that reversibly or irreversibly inhibit the catalytic activity of enzymes. Enzyme inhibition generally works in one of four ways in a biological system: a) by allosteric inhibition (inhibition carried out early in a biochemical pathway; the final product is bound to a modulator site that closes the active site by changing its shape, and when levels of the final product are reduced, the inhibitor disengages, re-enabling the synthetic pathway); b) by competitive inhibition (the inhibitor competes with the normal substrate for an enzyme's active site, and the level of inhibition is dependent on the relative concentrations of the substrate and the inhibitor); c) by uncompetitive inhibition (the inhibitor combines with the enzyme-substrate complex, preventing the complex from completing the reaction); and d) non-competitive inhibition (the inhibitor prevents dissolution of the enzyme-substrate complex by binding at a modifier site and effecting a deformation of the active site). Rudin, Norah, *Dictionary of Modern Biology*, Barron's Educational Series, Inc. (Hauppauge, N.Y.), 1997. Enzyme inhibitors can be administered or introduced into a biological system for any suitable and appropriate purpose, including for research purposes, diagnostic purposes or therapeutic purposes.

When enzyme inhibitors are being used for therapeutic purposes, they are usually being administered to halt or moderate the production of a biomolecule or byproduct of the degradation and/or production of a biomolecule that, in its current concentration, can have a detrimental effect on the biological system. Enzyme inhibitors can be natural or synthetic—and the synthetic enzyme inhibitors often resemble the natural enzyme inhibitors from a chemical and/or activity perspective.

Enzyme inhibitors, however, can encounter problems when dealing with a family of enzyme isoforms or isoenzymes. As used herein, the terms "isoform" and "isoenzyme" can be used interchangeably and can be defined as a variant of an enzyme that exists in different structural forms within a single species. Each isoform or isoenzyme has the same substrate specificity, but often has different substrate affinities. The different isoforms or isoenzymes in a particular family of isoforms or isoenzymes all have the same or similar molecular weights but may differ in configuration or charge. Each isoform or isoenzyme of a particular family of isoforms or isoenzymes can be distinguished by appropriate analytical techniques, including electrophoresis and the corresponding detection instrumentation. It may be that one of the isoforms should be inhibited and not any of the other isoforms. And beyond that, it may be that a particular isoform is targeted to be knowingly and selectively inhibited or "switched off".

Nitric oxide synthases (NOS) catalyze the oxidation of an L-arginine guanidinium nitrogen atom to nitric oxide (NO), a potent biological signaling molecule that mediates a diverse range of physiological processes within the cardiovascular, immune and nervous systems (S. Moncada et. al. 1991. Pharmacol. Review 43, 109; J. L. Dinerman et. al. 1993. Circ. Res. 73, 217 and J. F. Kerwin Jr. et. al. 1995. J.

Med. Chem. 38, 4343). Three mammalian NOS isoforms, nNOS (neuronal nitric oxide synthase: a constitutively expressed isoform located in neuronal tissue and involved in neurotransmission and long-term potentiation); eNOS (endothelial nitric oxide synthase: a constitutively expressed isoform which is involved in the regulation of smooth muscle relaxation and vascular tone); and iNOS (inducible nitric oxide synthase: the isoform in activated macrophage cells that plays a key role in normal immune responses by functioning as a cytotoxic agent), share a common modular architecture consisting of the active site heme domain where L-arginine and the essential cofactor, tetrahydrobiopterin, bind. The C-terminus of the heme domain is connected via a calmodulin-binding linker to the FMN/FAD domain, which shuttles electrons from NADPH to the heme domain (O. W. Griffith and D. J. Stuehr, 1995. Ann. Rev. Physiol. 57, 707 and B. S. Masters et al., 1996. FASEB J. 10, 552). The isoforms of NOS share only approximately 50% primary sequence homology, which suggests that they may differ from each other in regulatory aspects; however, there is very high sequence identity across species. (H. Huang et al, 2000. J. Med. Chem., 43, 2938–2945; J-M Hah et al, 2001. J. Med. Chem., 44, 2667; R. B. Silverman et al, 1997. J. Med. Chem., 40, 2813–2817; H. Huang et al, 1999. J. Med. Chem., 42, 3147, which are all incorporated herein in their entirety).

The over and under production of NO contributes to a large number of pathological conditions (S. Moncada et. al. 1991. Pharmacol. Review 43, 109; J. L. Dinerman et. al. 1993. Circ. Res. 73, 217 and J. F. Kerwin Jr. et. al. 1995. J. Med. Chem. 38, 4343). Hyperactivity by iNOS and nNOS leads to locally high, cytotoxic concentrations of NO and has been identified as a cause of a number of human diseases. Chronic neuro-degenerative diseases such as Alzheimer's, Parkinson's, and Huntington's correlate with overproduction of NO (V. L. Dawson and T. M. Dawson, 1998. Prog. Brain Res. 118, 215). In addition, chronic inflammatory diseases such as arthritis (C. O. Bingham 3rd., 2002. J. Rheumatol. Suppl. 65, 3) and colitis (C. H. Cho, 2001. J. Physiol. Paris, 95, 253) are directly linked to NO overproduction. The hypotension experienced during septic shock, the death of insulin producing pancreatic cells and the extensive cell death that occurs following stroke are likewise due to excessive production of NO (9). On the other hand, impaired NO production by eNOS results in endothelial dysfunction which is responsible for disease states such as hypertension (S. Taddei et al, 2001. J. Cardiovasc. Pharmacol. 38, Suppl. 2, S11) and atherosclerosis (B. S. Sachais, 2001. Curr. Atheroscler. Rep. 3, 412; E. A. Rekka and N.C. Chrysselis, 2002. Mini Rev. Med. Chem. 2, 433). As a result, the identification of isoform-selective NOS inhibitors is important in, for example, decreasing the production of NO by nNOS to minimize neuronal degeneration, but not affect the critical role eNOS plays in regulating blood pressure.

Thus, there remains a need in the art for the development of new treatments for inhibiting nNOS or otherwise preventing or deterring NO overproduction.

SUMMARY OF THE INVENTION

Applicant has discovered that crystal structures of three known nNOS selective dipeptide amide/peptidomimetic inhibitors complexed to both nNOS and eNOS, and the present invention provides methods for designing novel and selective potent inhibitors of the neuronal isoform on the basis of this newly discovered process.

In accordance with the present invention, there are provided novel compositions which inhibit nNOS, such compositions having the general Formula I, as follows:

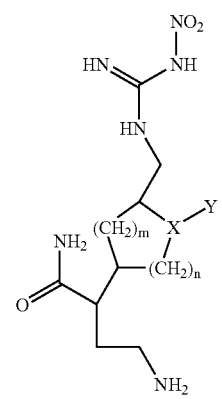

I where m and n each are at least 1 and m+n is from 2 to 4; X is CH or N and Y is $NH_2$, H or Alkyl, with the proviso that when X is CH then Y is $NH_2$ and when X is N then Y is H or Alkyl. Furthermore, Formula I exhibits several chiral centers and therefore for the purpose of this invention all stereoisomers and racemates are covered. In preferred embodiment, X is CH, Y is $NH_2$, m and n are 1 (cyclopentane ring) and m is 2 and n is 1 (cyclohexane ring), for example,

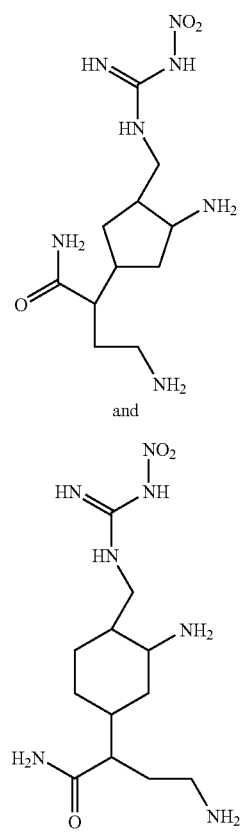

Additionally, when X is CH and Y is NH$_2$ and each m and n is 1 the cyclopentane ring may contain up to two double-bonds to afford a cyclopentadiene ring, for example,

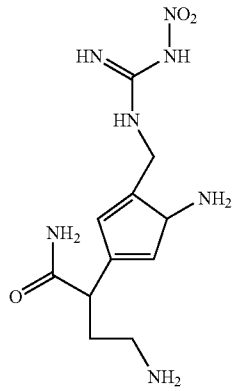

In another embodiment of the invention, when X is CH, Y is NH$_2$, m is 2 and n is 1, i.e. the ring is six membered, i.e. cyclohexane, any two carbons in the ring may be bridged by up to two carbon atoms, a —O— group or a —NR— group, where R is H or lower alkyl. The partial structures for these are shown below:

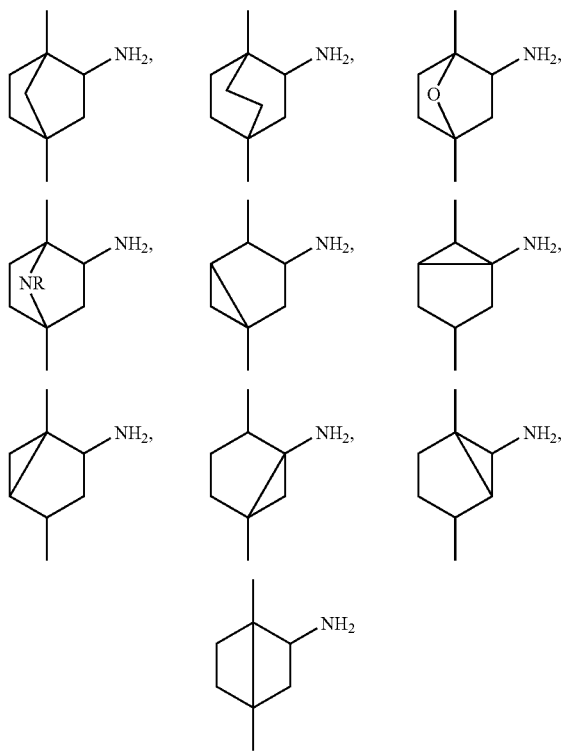

Yet in another embodiment of the invention, the amino group of the amide in Formula I may be replaced by a hydrogen atom resulting in an aldehyde, which may cyclize to form a five membered heterocyclic ring, which may be saturated or unsaturated.

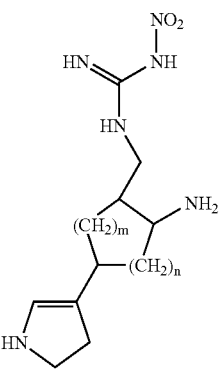

Yet, in another embodiment, when m is 1 or 2, n is 1, X is CH and Y is NH$_2$, the most preferred stereoisomer is one in which the amino group on the ring is tetrahedral, i.e. on a SP$^3$ carbon and trans to the guanidinomethyl group as shown below in the partial structure for the cyclohexane derivative:

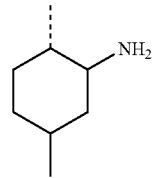

Yet in another embodiment, X is N, Y is H or Alkyl, m and n are 1. The following structure illustrates this embodiment.

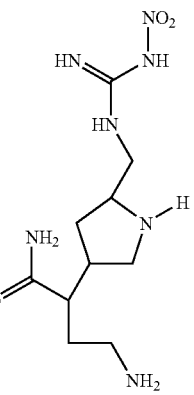

DETAILED DESCRIPTION AND EXAMPLES

Figure 1A:
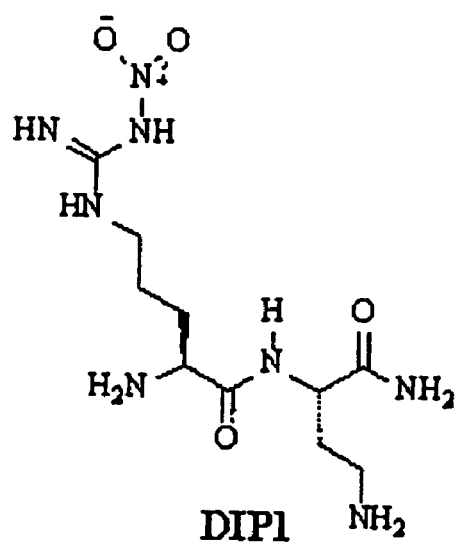
FIG. 1A shows the chemical structures of three dipeptide amide/peptidomimetic NOS inhibitors.
Figure 1A:
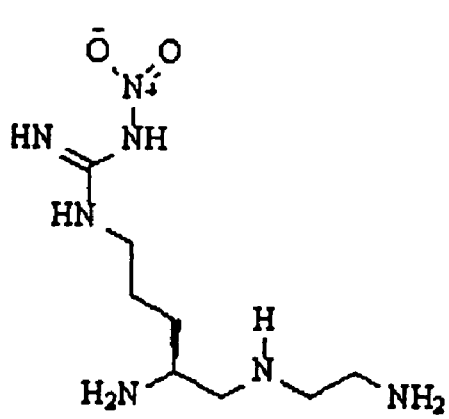
Figure 1A:
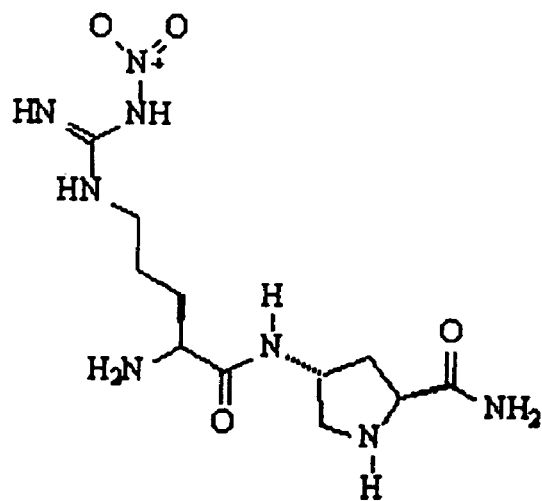

The present invention provides novel compounds that selectively inhibit neuronal Nitric Oxide Synthase (nNOS) over other isoforms of this enzyme. nNOS catalyzes the oxidation of a nitrogen atom of the guanidinium group of L-arginine to nitric oxide (NO), a potent biological signaling molecule that mediates a diverse range of physiological processes within the cardiovascular, immune and nervous system. Thus, by inhibiting nNOS, the compounds of the presnet invention are useable to treat or prevent disorders in human or veterinary patients that are caused, mediated or agrevated by NO within the body.

Detailed information relating the the biosynthesis of NO and the role of nNOS relative to other isoforms of the enzyme is found in Moncada, S. et. Al. *Nitric Oxide: Physiology, Pathophysiology, and Pharmacology*; Pharmacological Reviews, Vol. 43, no. 2, Pages 109–142 (1991); Hash, Jung-Mi et al., *Reduced Amide Bond Peptidomimetics. (4S)-N-(4-Amino-5-[aminoalkyl]aminopentyl)-N-nitroguanidines, Potent and Highly Selective Inhibitors of Neuronal Nitric Oxide Synthetase*, J. Med. Chem. Vol. 44, Pages 2667–2670 (2001); Huang, Hui, et al., $N^{\omega}$-*Nitroarginine-Containing Dipeptide Amides, potent and Highly Selective Inhibitiors of Neuronal Nitric Oxide Synthase*; J. Med. Chem, Vol. 42, Pages 3147–3153 (1999); Silverman, R. B., et al., *Selective Inhibition of Neuronal Nitric Oxide Synthase by N-Nitroargininine and Phenylalanine-Containing Dipeptides and Dipeptide Esters*, J. Med. Chem., Vol. 40, Pages 2813–2817 (1997) and Huang, Hui et al., *Synthesis and Evaluation of Peptidomimetics as Selective Inhibitors and Active Site Probes of Nitric Oxide Synthases*, J. Med. Chem, Vol. 43, Pages 2938–2945 (2000).

Applicant has discovered that crystal structures of three known nNOS selective dipeptide amide/peptidomimetic inhibitors complexed to both nNOS and eNOS, and the present invention provides methods for designing novel and selective potent inhibitors of the neuronal isoform on the basis of this newly discovered process.

Novel nNOS inhibiting componds of the present invention have the general Formula I, as follows:

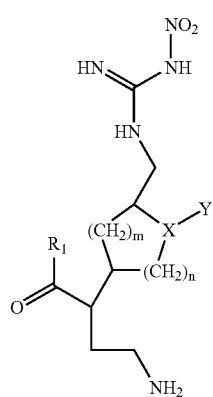

where m and n each are at least 1 and m+n is from 2 to 4; X is CH or N and Y is $NH_2$, H or Alkyl, with the proviso that when X is CH then Y is $NH_2$ and when X is N then Y is H or Alkyl $R_1$ is H or $NH_2$. Furthermore, Formula I exhibits several chiral centers and therefore for the purpose of this invention all stereoisomers and racemates are covered. In preferred embodiment, X is CH, Y is $NH_2$, m and n are 1 (cyclopentane ring) and m is 2 and n is 1 (cyclohexane ring), for example,

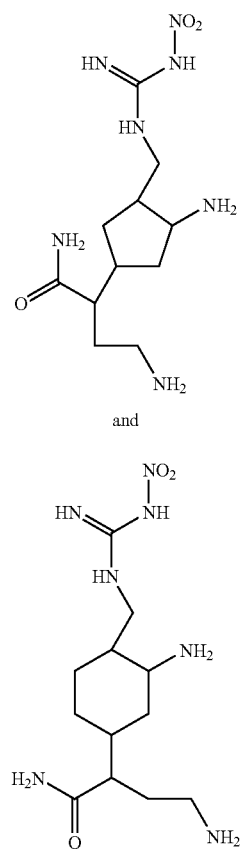

Additionally, when X is CH and Y is $NH_2$ and each m and n is 1 the cyclopentane ring may contain up to two double-bonds to afford a cyclopentadiene ring, for example,

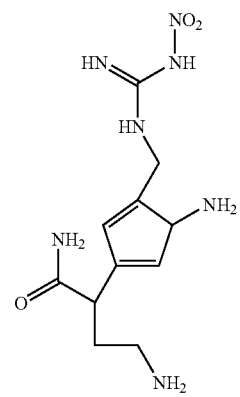

In another embodiment of the invention, when X is CH, Y is NH$_2$, m is 2 and n is 1, i.e. the ring is six membered, i.e. cyclohexane, any two carbons in the ring may be bridged by up to two carbon atoms, a —O— group or a —NR— group, where R is H or lower alkyl. The partial structures for these are shown below:

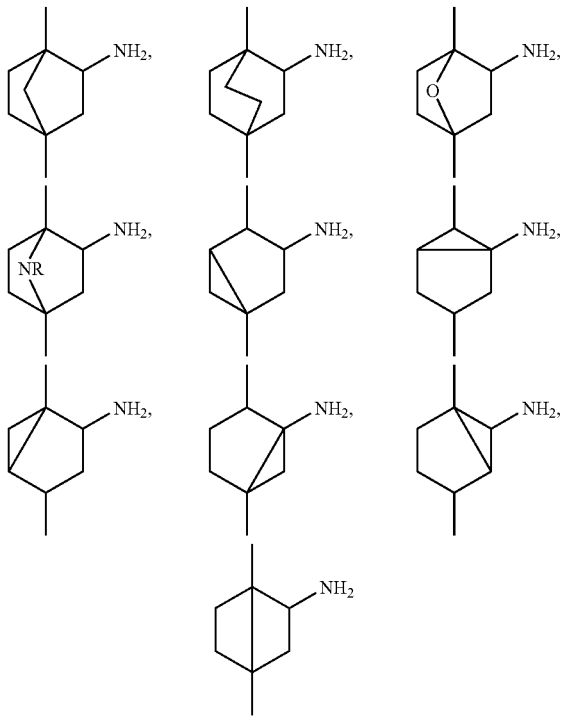

Yet in another embodiment of the invention, the amino group of the amide in Formula I may be replaced by a hydrogen atom resulting in an aldehyde, which may cyclize to form a five membered heterocyclic ring, which may be saturated or unsaturated.

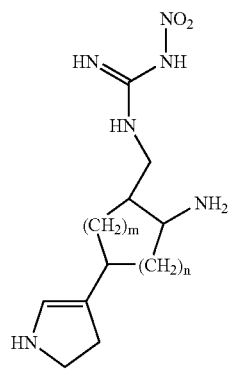

Yet, in another preferred embodiment, when m is 1 or 2, n is 1, X is CH and Y is NH$_2$, the most preferred stereoisomer is one in which the amino group on the ring is tetrahedral, i.e. on a SP$^3$ carbon and trans to the guanidinomethyl group as shown below in the partial structure for the cyclohexane derivative:

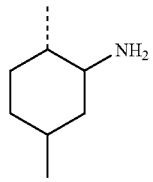

Yet in another preferred embodiment, X is N, Y is H or Alkyl, m and n are 1. The following structure illustrates this embodiment.

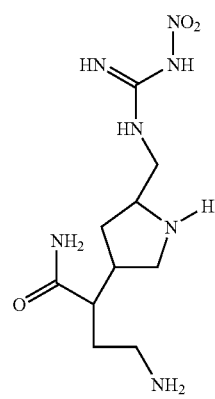

The present invention also includes prodrugs of the above-described compounds of this invention, such as prodrug derivatives of the amino and guanidine functions. The preparation of prodrugs of amino and guanidino functions is well known in the art (Hans Bundgaard, 1985. Design of Prodrugs, Elsevier Science Pub. Co., New York and Roger G. Melton and Richard J. Knox, Ed. 1999. Enzyme-prodrug strategies for cancer therapy, Kluwer Academic/Plenum Publishers, New York). These prodrugs are useful when delivery across membranes is necessary, particularly for therapeutic applications in central nervous system where drugs need to cross the blood barrier to exert their pharmacological action.

Referring now to the accompanying figures, FIG. 1A shows the chemical structures of three dipeptide amide/peptidomimetic NOS inhibitors of the present invention, namely: DIP1, L-N$^\square$-nitroarginine-2,4-L-diaminobutyramide; DIP2, (4S)-N-(4-amino-5-[aminoethyl]aminopentyl)-N'-nitroguanidine; DIP3, L-N$^\square$-nitroarginine-(4R)-amino-L-proline amide.

Figure 1C:
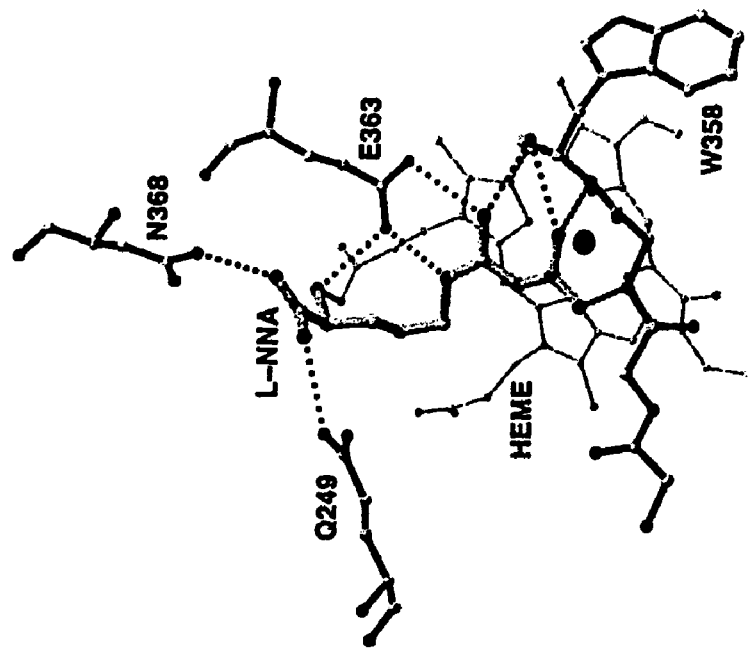
FIG. 1C is a stereo diagram of L-NNA bound in the active site of eNOS.
Figure 1B:
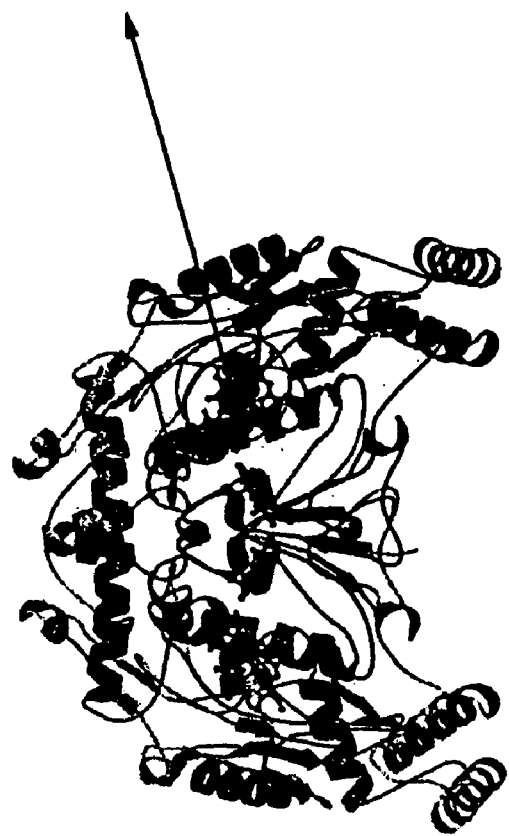
FIG. 1B is a ribbon diagram of eNOS heme domain.
Figure 2C:
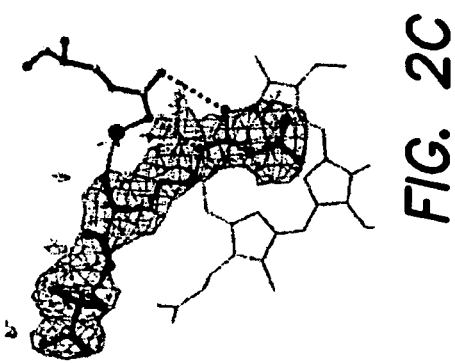
FIGS. 2A–2F are omit electron density maps contoured at 3σ of the three dipeptide amide/peptidomimetic inhibitors DIP1, DIP2, and DIP3 bound, respectively, to eNOS (2A, 2B,2C) and nNOS (2D,2E,2F), and dipeptide amide DIP1 bound to the D597N nNOS mutant (FIG. 2G).
Figure 2B:
Figure 2A:
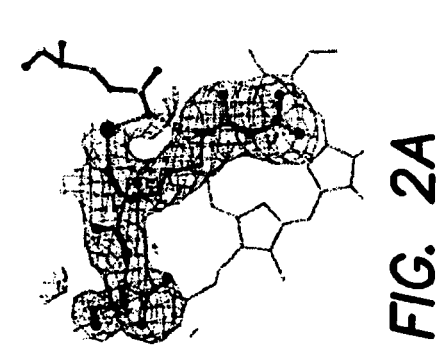
Figure 2G:
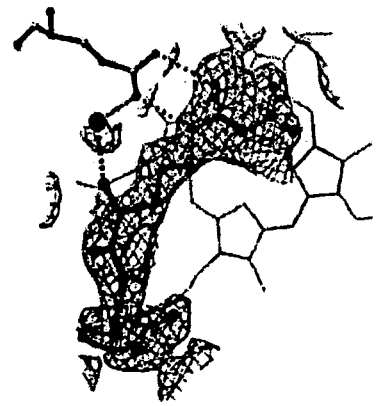
Figure 2F:
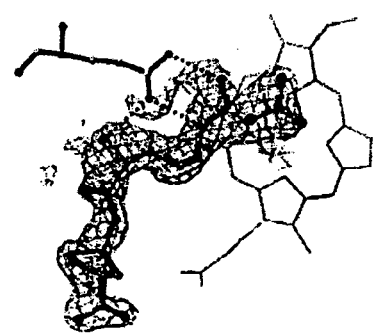
Figure 2E:
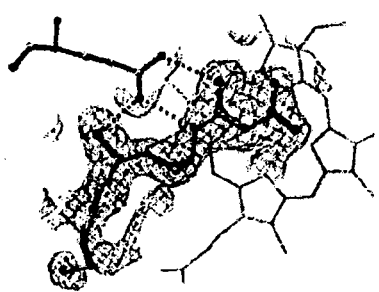
Figure 2D:
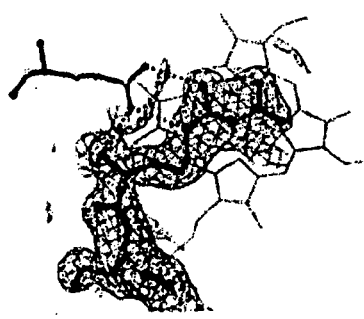

FIG. 1B is a ribbon diagram of eNOS heme domain. All three isoforms share the similar dimeric fold and possess a wide open solvent accessible channel connecting the heme active site to the molecular surface.

FIG. 1C is a stereo diagram of L-NNA bound in the active site of eNOS. An extensive hydrogen bonding network (dashed lines) between L-NNA and enzyme may explain its low nM potency, as described herebelow. However, a single amino acid difference, Asn$^{368}$ in eNOS and Asp$^{597}$ in nNOS, has little influence on L-NNA binding affinity.

FIGS. 2A–2F are omit electron density maps contoured at 3σ of the three dipeptide amide/peptidomimetic inhibitors DIP1, DIP2, and DIP3 bound, respectively, to eNOS (2A, 2B,2C) and nNOS (2D,2E,2F), and dipeptide amide DIP1 bound to the D597N nNOS mutant (G). Note the extended ligand conformation in eNOS and the D597N nNOS mutant structures, but the curled conformation in wild type nNOS.

Figure 3A:
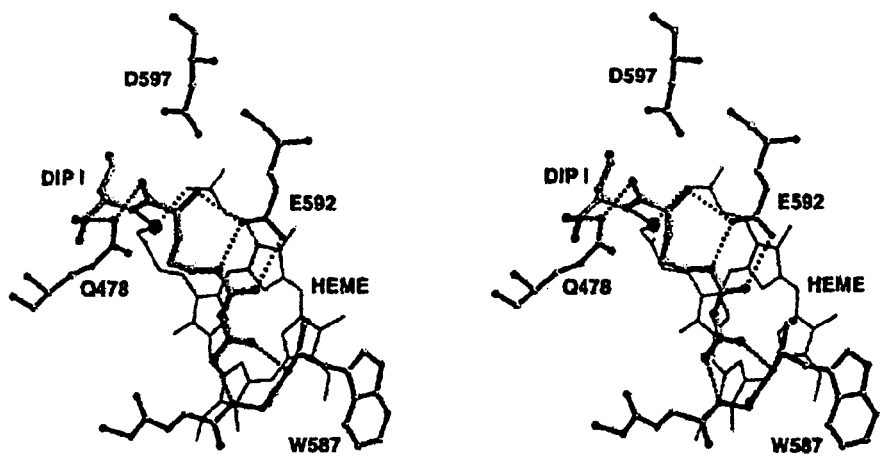
FIGS. 3A–3C are stereo diagrams of dipeptide amide DIP1 bound to the active site of (3A) wild type nNOS, (3B) wild type eNOS, and (3C) the D597N nNOS mutant.
Figure 3B:
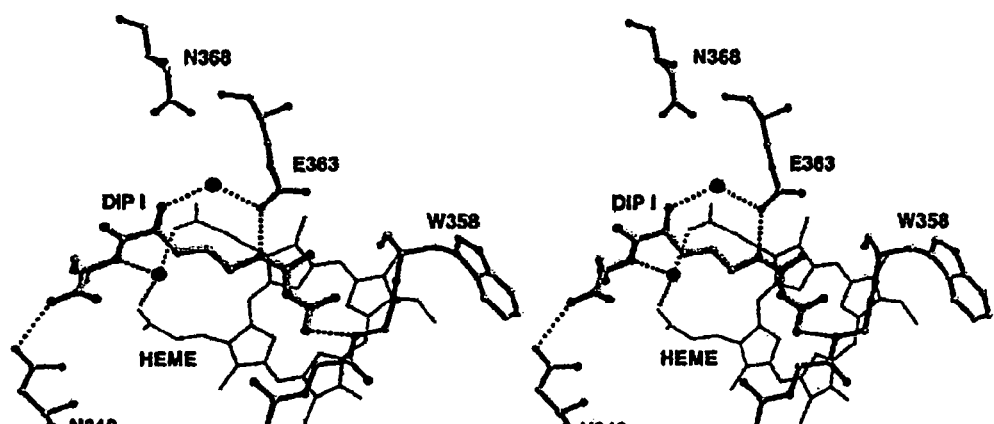
Figure 3C:
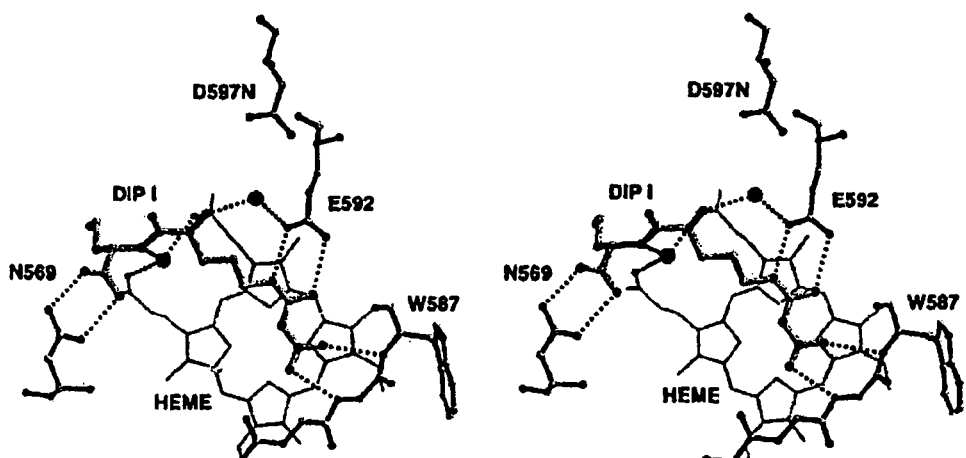

FIGS. 3A–3C are stereo diagrams of dipeptide amide DIP1 bound to the active site of (A) wild type nNOS, (B) wild type eNOS, and (C) the D597N nNOS mutant. Only the protein residues that make direct contact with the inhibitor are shown. Hydrogen bonds are denoted by dashed lines. When dipeptide amide DIP1 adopts an extended conformation, a water molecule bridges between the α-amino group of the ligand and the active site glutamate residue (Glu$^{363}$ of eNOS or Glu$^{592}$ of nNOS), whereas a curled conformation retains a direct hydrogen bond between the α-amino group of the ligand to Glu$^{592}$ in wild type nNOS. Another water molecule was consistently observed in structures which bridges between the peptide bond nitrogen of DIP1 and heme propionate. Contacts from the C-terminal amide to the surrounding protein residues vary depending on the ligand binding mode.

The crystal structures of the heme domain for all three isoforms now are known, which opens the way for structure-based inhibitor design. With NOS, the structures are very similar, including the highly conserved active site (FIG. 1). For example, L-N$^\omega$-nitroarginine (L-NNA) is a potent inhibitor of NOS but exhibits poor selectivity. This is understandable since all three NOS isoforms possess a binding pocket that specifically recognizes L-arginine. When L-NNA binds to nNOS, the amino and carboxylate groups attached to the α-carbon bind exactly as in the L-arginine complex (FIG. 1). The only difference between eNOS and nNOS is that the carboxylate group of L-NNA is within hydrogen bonding distance of Asp$^{597}$ in nNOS while the corresponding residue in eNOS is Asn$^{368}$. However, L-NNA inhibitory potency to eNOS is no better than that to nNOS. This implies that the Asp$^{597}$/Asn$^{368}$ difference is insignificant to the ligand binding affinity compared to the extensive hydrogen bonding networks between L-NNA and the surrounding protein environment. This argument is also supported by the fact that L-arginine exhibits similar $K_m$ values in the low μM range for all three NOS isoforms.

Thus there was, until the present invention, no obvious structural difference between isoform active sites that could be exploited for structure-based design efforts. Nevertheless, prior to the reported crystal structures various isoform-selective inhibitors of NOS were identified. Some of the most important ones are a number of non-biological dipeptide amides and peptidomimetics built on the L-NNA scaffold (FIG. 1A) that show 1500-fold or better selective inhibition of nNOS over eNOS (22–24). To uncover the structural basis for why the dipeptide amide/peptidomimetic inhibitors shown in FIGS. 1A, 1B and 1C exhibit a selectivity toward nNOS over eNOS while L-NNA does not, Applicant solved the crystal structures of the inhibitors shown in FIGS. 1A, 1B and 1C, with each each bound to nNOS and eNOS (FIG. 4). The binding of the nitroguanidine of all three dipeptide amides/peptidomimetic to nNOS (FIG. 2) follows the paradigm seen previously for NOS binding of arginine analogues, as well as amidine and thiourea-based inhibitors (27,28) in that the guanidine or guanidine mimic makes a bifurcated hydrogen bonding interaction to a conserved active-site glutamate, Glu$^{592}$. The presence of the N-nitro group strengthens this anchoring interaction to nNOS by providing two additional hydrogen bonds to the protein backbone (FIG. 3A). In eNOS the dipeptide amides/peptidomimetic have the nitroguanidine positioned similarly above the heme, but in all three structures either the terminal guanidino-to-glutamate Glu$^{363}$ hydrogen bond or the nitro-to-backbone hydrogen bond (or both) is stretched slightly beyond a favorable distance (FIGS. 2A–2C, and 3B).

The largest and most significant difference between eNOS and nNOS is that in eNOS the nitroarginine side chain of all three inhibitors adopts a fully extended conformation while in nNOS, the side chain curls (FIG. 2). This difference places the α-amino group of I in position to form a direct hydrogen bond with Glu$^{592}$ in nNOS (FIG. 3A). In eNOS the extended conformation of the inhibitors places the α-amino group too far for direct hydrogen bonding and instead, a water molecule bridges between the inhibitor α-amino group and Glu$^{363}$ (FIG. 3B).

The obvious correlation between tight binding to nNOS and the curled binding mode of the dipeptide amide/peptidomimetic inhibitors strongly suggested that if we could identify the driving force that bends each ligand into the curled conformation, then we would find the structural basis of the observed isoform selectivity. We looked first to the C-terminus of the dipeptide amide/peptidomimetic inhibitors. Owing to the absence of a carboxylate on C a and to the presence of an extended C-terminal portion, the dipeptide amides/peptidomimetic vacate the amino acid binding pocket and instead point into the solvent accessible channel. Surprisingly, we found that in all six complexes every residue in this region that makes direct contact with the ligand is conserved between nNOS and eNOS. Although the C-terminal portion of the dipeptide amide/peptidomimetic makes different contacts in nNOS and eNOS (FIG. 3), the same contacts are available to the ligands in either protein environment. This indicates that in the nNOS context the dipeptide amides/peptidomimetic are performing their conformational acrobatics to satisfy some especially favorable contact that does not involve the dipeptide amide/peptidomimetic C-terminal tail and is not present in eNOS.

Therefore, we looked in the vicinity of the dipeptide amide/peptidomimetic α-amino group where the isoform variant residue Asn$^{368}$/Asp$^{597}$ (eNOS/nNOS) lies in the vacant carboxylate binding pocket 6.5 Å from the conserved active site glutamate, Glu$^{363}$/Glu$^{592}$ (eNOS/nNOS). The curl of the dipeptides in nNOS juxtaposes the α-amino group between the two negatively charged side chains, Glu$^{592}$ and Asp$^{597}$. We hypothesized that in nNOS the inhibitors adopt the curled conformation in order to place the α-amino group in position for maximum electrostatic stabilization of the Asp$^{597}$ and Glu$^{592}$ negative charges. Such stabilization is not possible in eNOS because Asn$^{368}$ does not bear a negative charge.

We next tested this hypothesis by producing D597N nNOS and N368D eNOS mutant proteins. The crystal structure of the D597N mutant complexed with dipeptide amide I (FIGS. 2G and 3C) clearly shows that the inhibitor switches to the extended conformation and has a water molecule bridging between the inhibitor α-amino group and Glu$^{592}$, exactly as in wild type eNOS. Consistent with the structure analysis, the inhibitory potency of the dipeptide amides/peptidomimetic dropped 216–225 fold due to this single site mutation in nNOS, with $K_i$ values (μM) of dipeptide amides/peptidomimetic compounds of FIGS. 1A, 1B and 1C changing from 0.303, 0.152, and 0.097 for the wild type nNOS to 67.0, 34.2, and 21.0 for the D597N nNOS mutant, respectively. Likewise, when Asn$^{368}$ is replaced with Asp in eNOS, dipeptide amide/peptidomimetic affinities increase 11–22 fold, with $K_i$ values (μM) of dipeptide amides/peptidomimetic compounds of FIGS. 1A, 1B and 1C being 9.5, 4.6, and 5.1 compared to 107.0, 80.0, and 110.0 for the wild type eNOS, respectively. Therefore, a single amino acid difference in the vacant carboxylate binding pocket of nNOS is responsible for more than two orders of magnitude selectivity for an L-NNA-containing dipeptide amide/peptidomimetic inhibitor even though neither Asp nor Asn lends selectivity to the binding affinity of L-NNA itself. This first direct insight into the structural basis for isoform-selective inhibition in NOS should be valuable in the future development of even more potent isoform-selective NOS inhibitors.

What is claimed is:

1. A composition of matter comprising a compound having the formula:

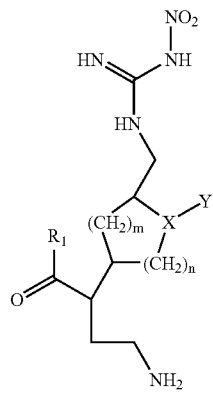

where m and n each are at least 1 and m+n is from 2 to 4; $R_1$ is H or $NH_2$; X is CH or N and Y is $NH_2$, H or Alkyl, with the proviso that when X is CH then Y is $NH_2$; when m is 2 and n is 1 any two carbons of the ring in which X is a substituent may be bridged by either i) up to two carbon atoms, ii) an —O— group or iii) an —NR— group in which R is either H or lower alkyl; and wherein, when m and n are both 1, the ring in which X Is a substituent may include two double bonds.

2. A composition according to claim 1 wherein the compound has the formula:

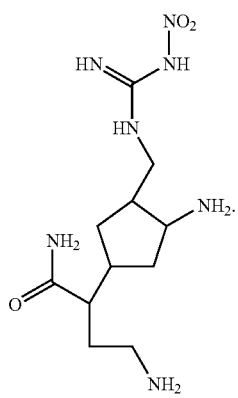

3. A composition according to claim 1 wherein the compound has the formula:

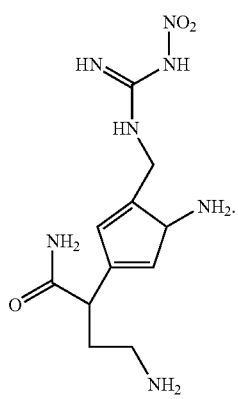

4. A composition according to claim 1 wherein the ring in which X is a substituent has a structural formula selected from the group consisting of:

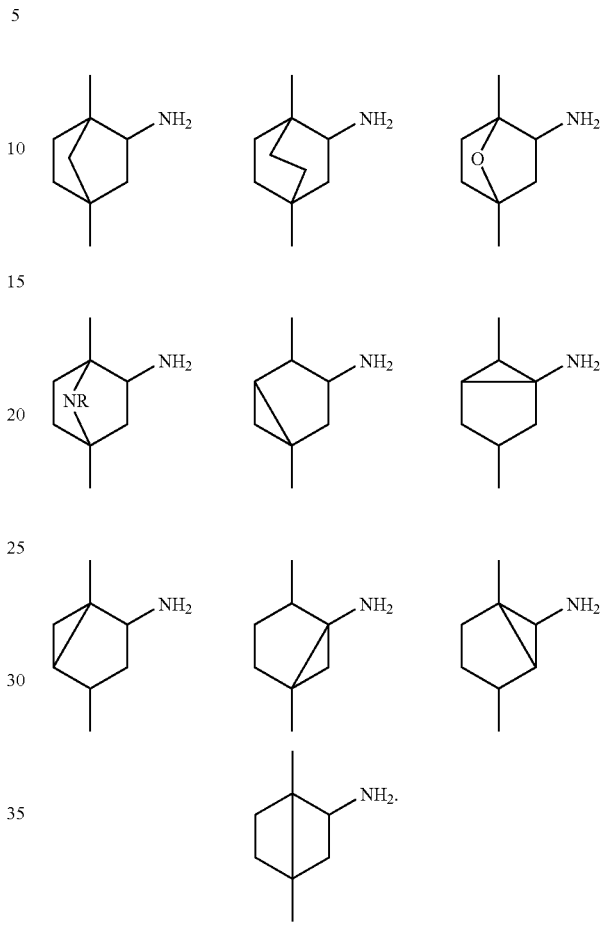

5. A composition according to claim 1 wherein $R_1$ is H.

6. A composition according to claim 1 wherein $R_1$ is H and wherein the aldehyde group formed by $R_1$ and the doubly bonded O is cyclized with the primary amine to form a saturated or unsaturated ring.

7. A composition according to claim 6 wherein the compound has the formula:

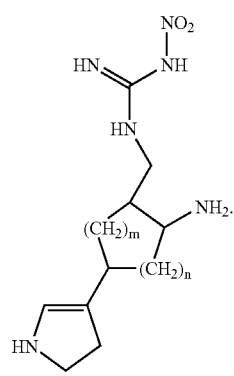

8. A composition according to claim 1 wherein m is 1 or 2, n is 1, X is CH and Y is NH$_2$.

9. A composition according to claim 8 comprising a stereoisomer wherein the amino group on the ring is tetrahedral and trans to the guanidinomethyl group.

10. A composition according to claim 1 wherein X is N, Y is H or Alkyl m is 1 and n is 1.

11. A composition according to claim 10 wherein the compound has the formula:

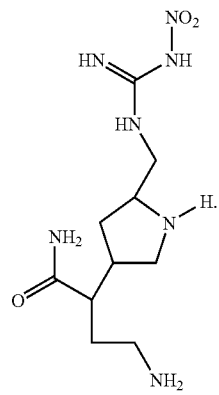

12. A method for inhibiting nNOS in a human or veterinary patient, said method comprising the step of administering to the patient a therapeutically effective amount of a composition of any one of claims 1–11.

13. A method for inhibiting nNOS in a human or veterinary patient, said method comprising the step of administering to the patient a prodrug that metabolizes to form a therapeutically effective amount of a composition of any one of claims 1–11.

14. A composition according to claim 1 wherein the compound has the formula:

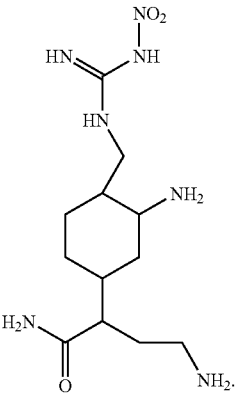

* * * * *